(12) United States Patent
Park et al.

(10) Patent No.: US 8,252,533 B2
(45) Date of Patent: Aug. 28, 2012

(54) METHOD FOR INCREASING EFFICIENCY OR SPECIFICITY OF HYBRIDIZATION BETWEEN PNA PROBES IMMOBILIZED ON SUPPORT AND TARGET NUCLEIC ACIDS

(75) Inventors: Heekyung Park, Daejeon (KR); Jaejin Choi, Daejeon (KR)

(73) Assignee: Panagene Inc., Daejeon (KR)

(*) Notice: Subject to any disclaimer, the term of this patent is extended or adjusted under 35 U.S.C. 154(b) by 218 days.

(21) Appl. No.: 12/449,692

(22) PCT Filed: Feb. 22, 2008

(86) PCT No.: PCT/KR2008/001068
§ 371 (c)(1),
(2), (4) Date: Jan. 27, 2010

(87) PCT Pub. No.: WO2008/103015
PCT Pub. Date: Aug. 28, 2008

(65) Prior Publication Data
US 2010/0184030 A1  Jul. 22, 2010

(30) Foreign Application Priority Data
Feb. 23, 2007  (KR) .................. 10-2007-0018384

(51) Int. Cl.
*C12Q 1/68* (2006.01)
*C12P 19/34* (2006.01)
*C12M 1/34* (2006.01)
*C12M 3/00* (2006.01)
*C07H 21/02* (2006.01)

(52) U.S. Cl. .... 435/6.1; 435/6.11; 435/91.1; 435/287.1; 435/287.2; 536/23.1

(58) Field of Classification Search .................. 435/6.1, 435/6.11, 6, 91.1, 183, 287.1, 287.2; 436/94; 536/23.1, 24.3, 24.33; 514/3.2
See application file for complete search history.

(56) References Cited

U.S. PATENT DOCUMENTS

| | | | | |
|---|---|---|---|---|
| 6,051,378 A | * | 4/2000 | Monforte et al. ............ | 435/6.12 |
| 6,436,638 B1 | * | 8/2002 | De Leon et al. ............ | 435/6.13 |
| 7,282,329 B2 | | 10/2007 | Manalis et al. | |
| 2004/0072208 A1 | | 4/2004 | Warthoe et al. | |
| 2007/0122824 A1 | * | 5/2007 | Tucker et al. ............... | 435/6 |

FOREIGN PATENT DOCUMENTS

| | | |
|---|---|---|
| KR | 10-2002-0080803 | 10/2002 |
| WO | 93/10263 | 5/1993 |
| WO | 02/16647 | 2/2002 |
| WO | 02/059137 | 8/2002 |
| WO | 02/083949 | 10/2002 |
| WO | 2008/103015 | 8/2008 |

OTHER PUBLICATIONS

G. Csako, "Present and future of rapid and/or high-throughput methods for nucleic acid testing", *Clinica Chimica Acta* 363 (2006) 6-31.

D. Wang et al., "Single nucleotide polymorphism discrimination assisted by improved base stacking hybridization using oligonucleotide microarrays", *BioTechniques* 35: 300-308 (Aug. 2003).

K. Kim et al., "Development and evaluation of a highly sensitive human papillomavirus genotyping DNA chip", *Gynecologic Oncology* 100 (2006) 38-43.

M. Mehlmann et al., "Optimization of fragmentation conditions for microarray analysis of viral RNA", *Analytical Biochemistry* 347 (2005) 316-323.

R. Peytavi et al., "Correlation between microarray DNA hybridization efficiency and the position of short capture probe on the target nucleic acid", *BioTechniques* vol. 39, No. 1 (2005), p. 89-96.

A. Syvanen, "Toward genome-wide SNP genotyping", *Nature Genetics Supplement* vol. 37, Jun. 2005, p. S5-S10.

A. Syvanen, "Accessing Genetic Variation: Genotyping Single Nucleotide Polymorphisms", *Nature* vol. 2, Dec. 2001, p. 930-942.

P. Nielson et al., "Sequence-Selective Recognition of DNA by Strand Displacement with a Thymine-Substituted Polyamide", *Science* 254, 1991, p. 1497-1500.

H. Stender et al., "PNA for rapid microbiology", *Journal of Microbiological Methods* 48 (2002) 1-17.

O. Brandt et al., "Peptide nucleic acids on microarrays and other biosensors", *Trends in Biotechnology* vol. 22, No. 12, Dec. 2004, p. 617-622.

F. Raymond et al., "Detection of target DNA using fluorescent cationic polymer and peptide nucleic acid probes on solid support", *BMC Biotechnology* 5:Apr. 10, 2005, p. 1-5.

B. Gaylord et al., "SNP detection using peptide nucleic acid probes and conjugated polymers: Applications in neurodegenerative disease identification", *PNAS* vol. 102, No. 1, Jan. 4, 2005, p. 34-39.

S. Ye et al., "Detection of single nucleotide polymorphisms by the combination of nuclease S1 and PNA", *Nucleic Acids Research Supplement* No. 2, 2002, p. 235-236.

M. Komiyama et al., "PNA for One-Base Differentiating Protection of DNA from Nuclease and Its Use for SNPs Detection", *J. Am. Chem. Soc.* 2003, 125, 3758-3762.

V. Vogt, "Purification and Properties of $S_1$ Nuclease from *Aspergillus*", *Methods in Enzymology*, 65, 248-255.

J. Wang, "DNA biosensors based on Peptide Nucleic Acid (PNA) recognition layers. A review", *Biosensors & Bioelectronics* 13 (1998) 757-762.

F. Uslu et al., "Labelfree fully electronic nucleic acid detection system based on a field-effect transistor device", *Biosensors and Bioelectronics* 19 (2004) 1723-1731.

(Continued)

*Primary Examiner* — Frank W Lu
(74) *Attorney, Agent, or Firm* — Clark & Brody

(57) ABSTRACT

Disclosed are a process for increasing efficiency or specificity of hybridization between peptide nucleic acid (PNA) probes immobilized on a support and target nucleic acids, which comprises the step of fragment the target nucleic acids to reduce the size of the target nucleic acids, or selectively degrading the target nucleic acids which mismatch with the PNA probes, in the hybridization reaction between the PNA probes supported on a support and the target nucleic acids; and a composition and a kit therefor.

10 Claims, 13 Drawing Sheets

OTHER PUBLICATIONS

J. Hahm et al., "Direct Ultrasensitive Electrical Detection of DNA and DNA Sequence Variations Using Nanowire Nansensors", *Nano Letters*, 2004, vol. 4, No. 1, p. 51-54.

A. Macanovic et al., "Impedance-based detection of DNA sequences using a silicon transducer with PNA as the probe layer", *Nucleic Acids Research*, 2004, vol. 32, No. 2, e20.

* cited by examiner

[Figure 1]
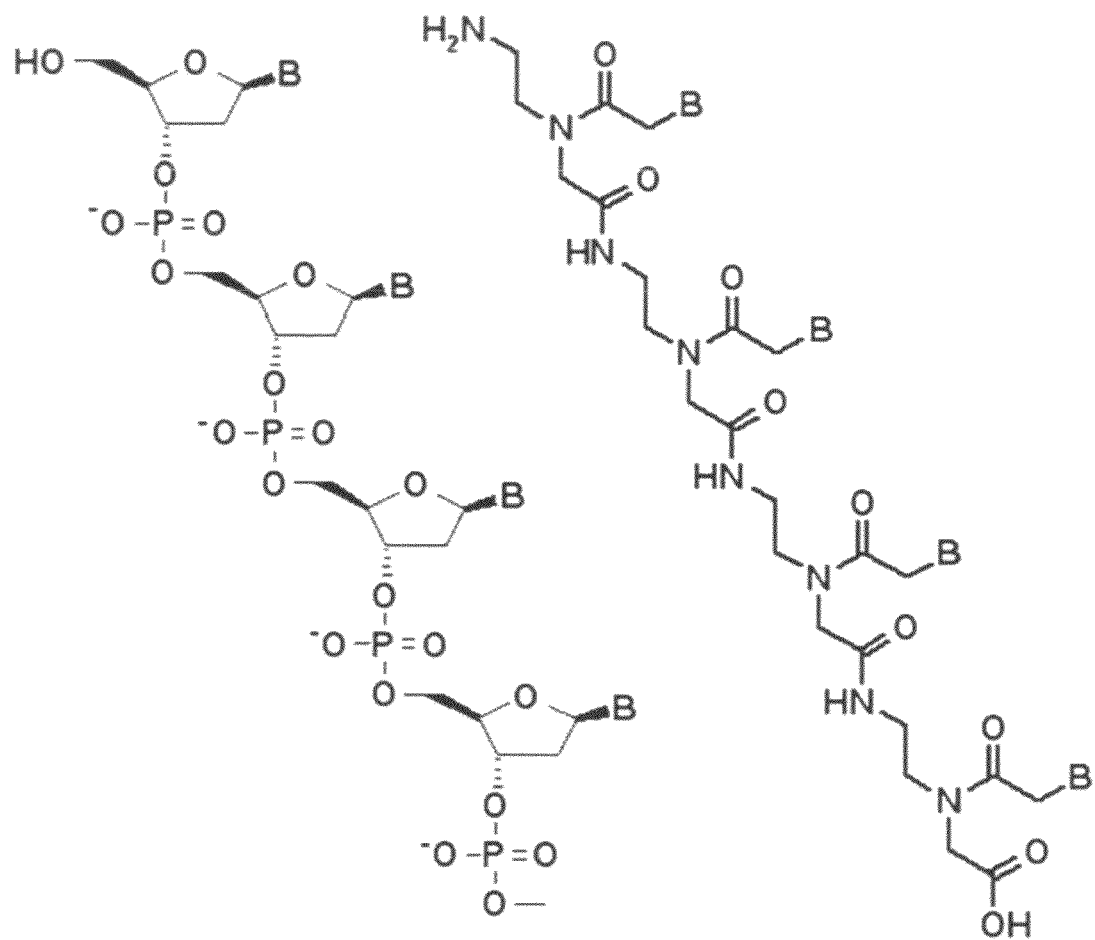
DNA                    PNA

[Figure 2]
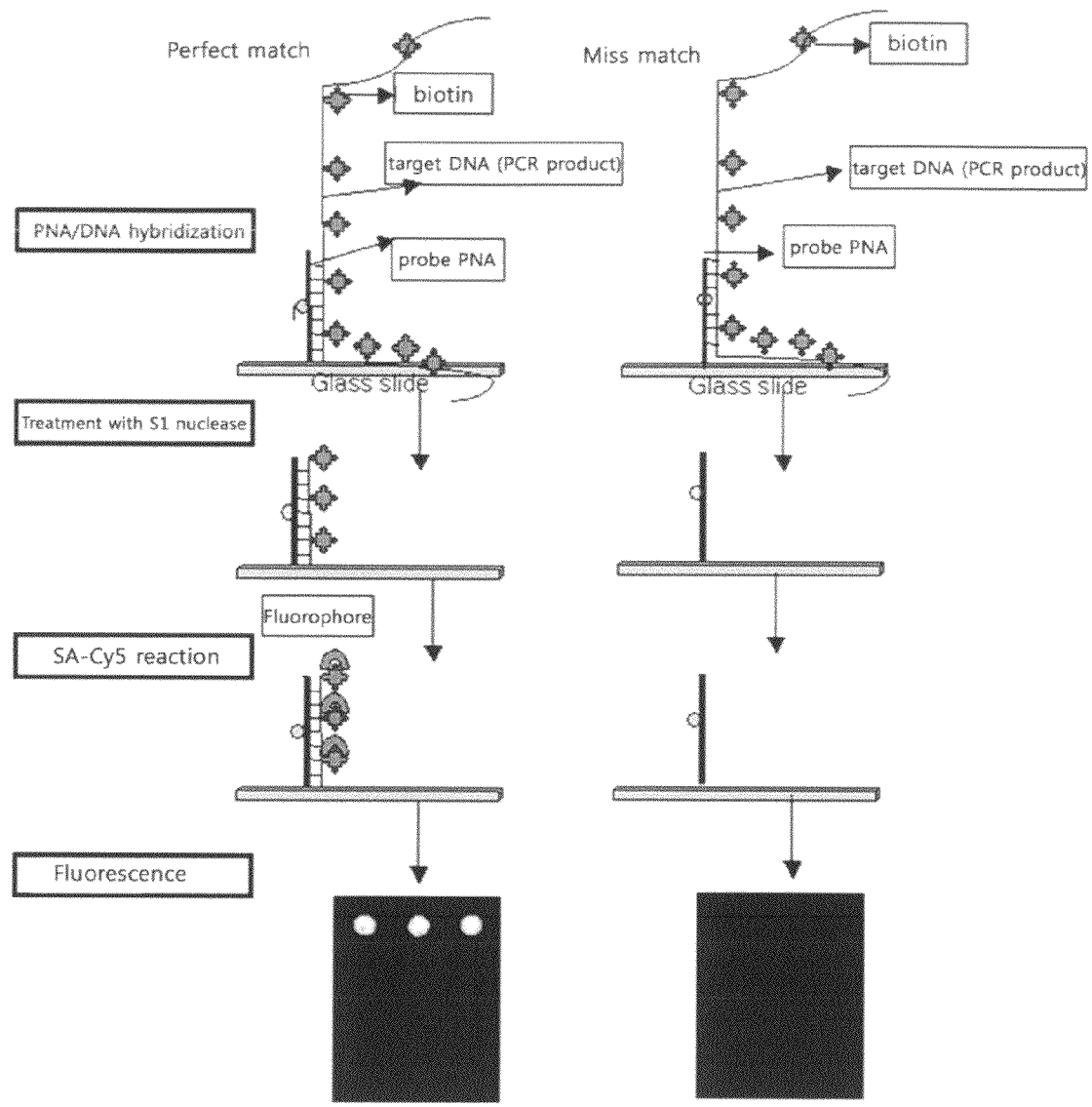

[Figure 3]
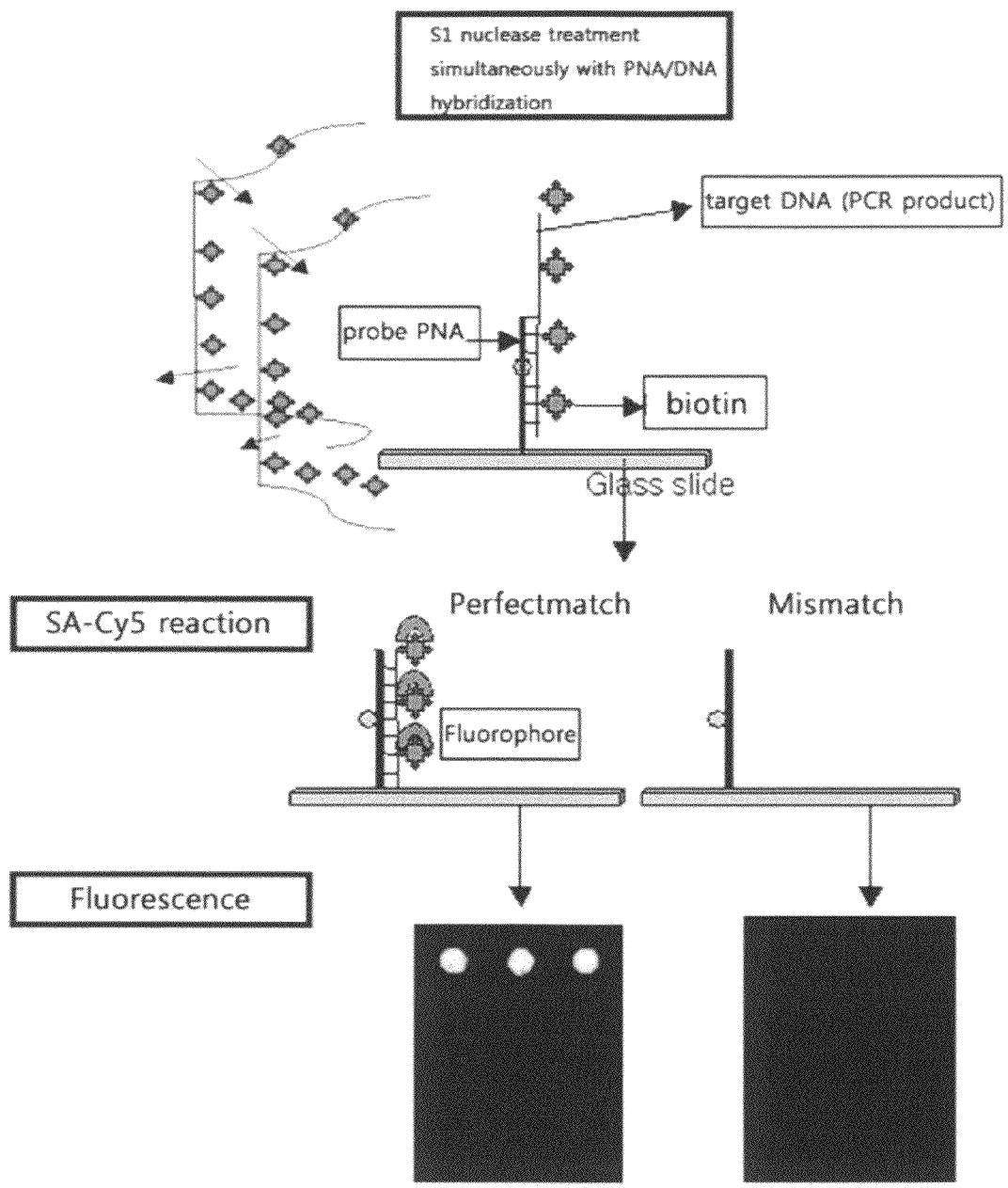

[Figure 4]

5' tgcaagtcgaacggtaacaggaagcagcttgctgctttgctgacgagttgcgaacgggtgagtaatgtct|ggaaaactgcctgatgagagggggataactactggaaacggtagctaataccgcataacgtcgca 3'
   49F-biotin                                                                                                                        AS98C                                                                                                182R-biotin
    (1)                                                                                         (2)                                                                         (3)

5' tgcaagtcgaacggtaacaggaagcagcttgctgctgtttgctgacgagtggcggacgggtgagtaatgtct|ggaaaactgcctgatgagtgggggataactactggaaacggtagctaataccgcataacgtcgcaagga
ccaaagagggggaccttcggcctcttgccatcggatgtgcccagatggattagctagtaggtggggtaaaggctcactaggcgacgatccctagctggtctgagaggatgaccagccacactgg
aactgagacacggtccagactcctacgggaggcagcagtggggaatattgcacaatgggcgcaagcctgatgcagccatgccgcgtgtatgaagaaggccttcgggttgtaaagtactttcagcggg
                                                                                  365R-biotin
                                                                                  (4)

5' tgcaagtcgaacggtaacaggaagcagcttgctgctttgctgacgagtggcggacgggtgagtaatgtct|ggaaaactgcctgatgagtgggggataactactggaaacggtagctaataccgcataacgtcgcaagga
ccaaagagggggaccttcggcctcttgccatcggatgtgcccagatggattagctagtaggtggggtaaaggctcactaggcgacgatccctagctggtctgagaggatgaccagccacactgg
aactgagacacggtccagactcctacgggaggcagcagtggggaatattgcacaatgggcgcaagcctgatgcagccatgccgcgtgtatgaagaaggccttcgggttgtaaagtactttcagcggg
aggaagggagtaaagttaatacctttgctcattgacgttacccgcagaagaagcaccggctaactcc 3'
                                   504R-biotin
                                     (5)

5' cggttcggttgaagagaaaaatctgaaatctgaactctgaaggtttgactctgaragagggaaaagcgtaatacgtaatacgccacctcgcgacatggactgaaagcgctcgcaactgctcttaacaattatcagtaat
ctgtgtgggcactcgaagatacggatcttcgacgtcgacctgccggccctaacacatgcaagtcgaacggtaatacacagtcaagtcgagaagtgaacacgtaattcattgaccatcaaagtttaaatgaagagttg
atcatgctcagattcaattactgaccttgcttgctgacgaggttgcggtcgagacagcatgacttgcttgctgaggtgcggcggctgagttgcggctgcatgggattagctagtaggtgggtaaagactca
ggggataactactggaaacggtagctaataccgcatgtggcggccaggccttaataccaaggaacacggtaatactgcttgatgcccctgccctcaggggagttgagtgccagcagagatgccagcagaggatgcatactgca
cctaggcgacgatccctagctggtctgagaggatgaccagccacactggaactgagacacggtccagactcctacgggaggcagcagtggggaatattgcacaatgggcgcaagcctgatgcagc
catgccgcgtgtatgaagaaggccttcggattgtaaagtactttgtacatcgagatatgaaagagaagcaccggctaac 3'
                                                                                759R-biotin
                (6)                                                                                  (5)
    759F-biotin 5' aagggtataaaagcgggttttgctgggggaatcaacagtcagcagtttcattttcattgccgcctcggaggaactcctctatatgcgcctccatcgacgaccgcccggatgtgaatcacttcaacaatg
cagccggttcggttgaagagaaaaatctgaaatctgaacttgacttgaragaggaaaagcgtaatacgccacctcgcgacatggactgaaagcgctcgcaactgctcttaacaattatcag
acaatctgtgtgggcactcgaagatacggatcttcgacgtcgaagacaatggaataccaagttcaggagtgaacacgtaattcattgaccatcaaactttaaattgaag
agtttgatcatgctcagattcaattactgaccttgcttgctgacgagttgcggtcgagaggtgaggttgcggcggctgagtggcggctgcatgggatttagctagtaggtagggtaaaggtaaag
atgaggggataactactggaaacggtagctaataccgcatgtggaagaccaaaagagggaccttcggtctcttacccaccctacggaggcagcagtggggatattgcacaatgggcgcaagcctgat
gcagccatgccgcgtgtatgaagaaggccttcgggttgtaaagtactttcagcggggaggaagggagtaaagttaatacctttgctcattgacgttacccgcacaagaagcaccggctaactccgtgcc
agcagccgcggtaatacggagggtgcaagcgttaatcggaattactgggcgtaaagcgcacgcaggcggtttgttaagtcagatgtgaaatccccgg 3'
                                                                                 1000R-biotin
   (7)                                                                                  (8)
1000F-biotin

[Figure 5]
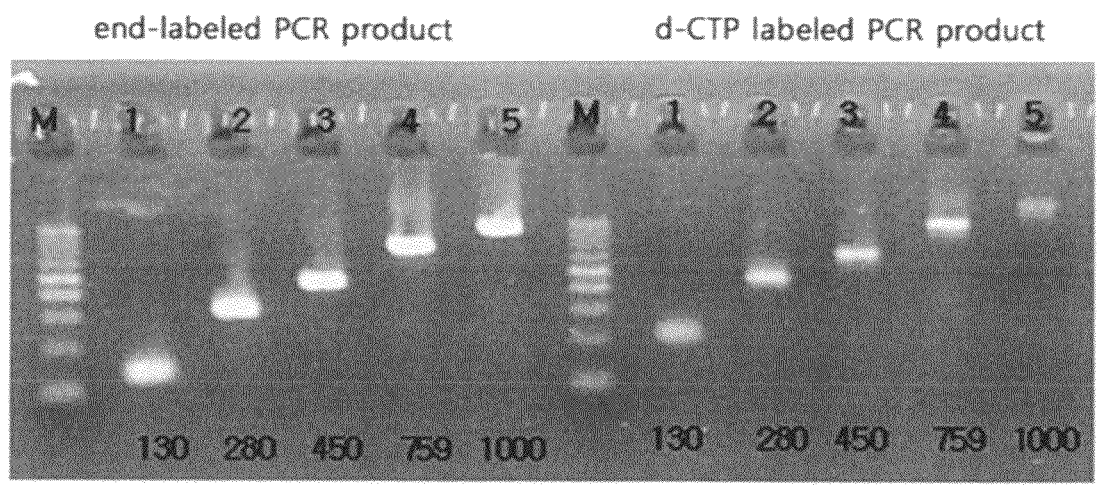
M: 100bp ladder
1: 130bp target nucleic acid
2: 280bp target nucleic acid
3: 450bp target nucleic acid
4: 759bp target nucleic acid
5: 1000bp target nucleic acid

[Figure 6]
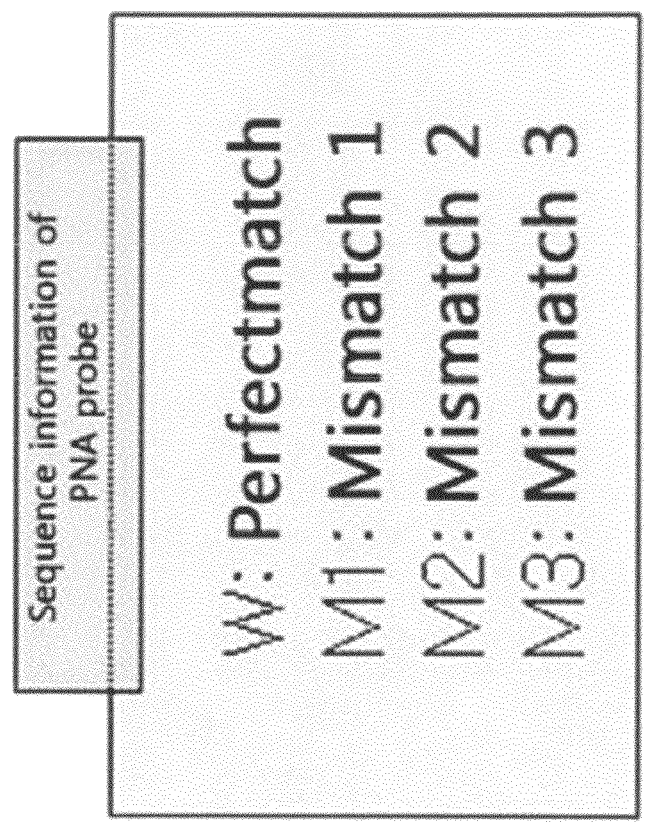
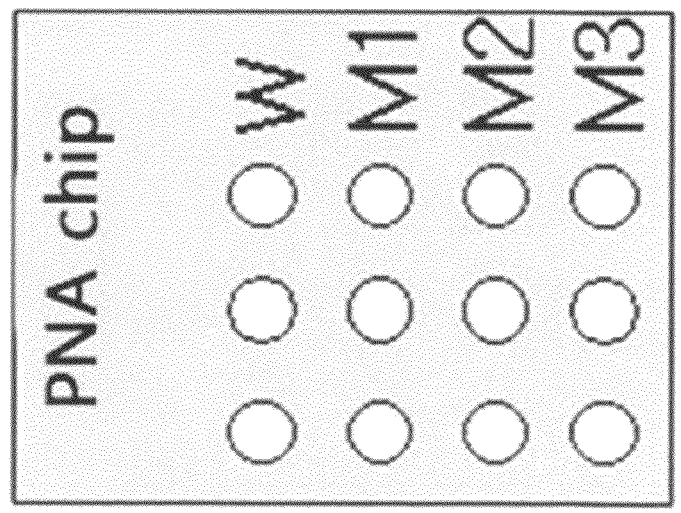

[Figure 7]
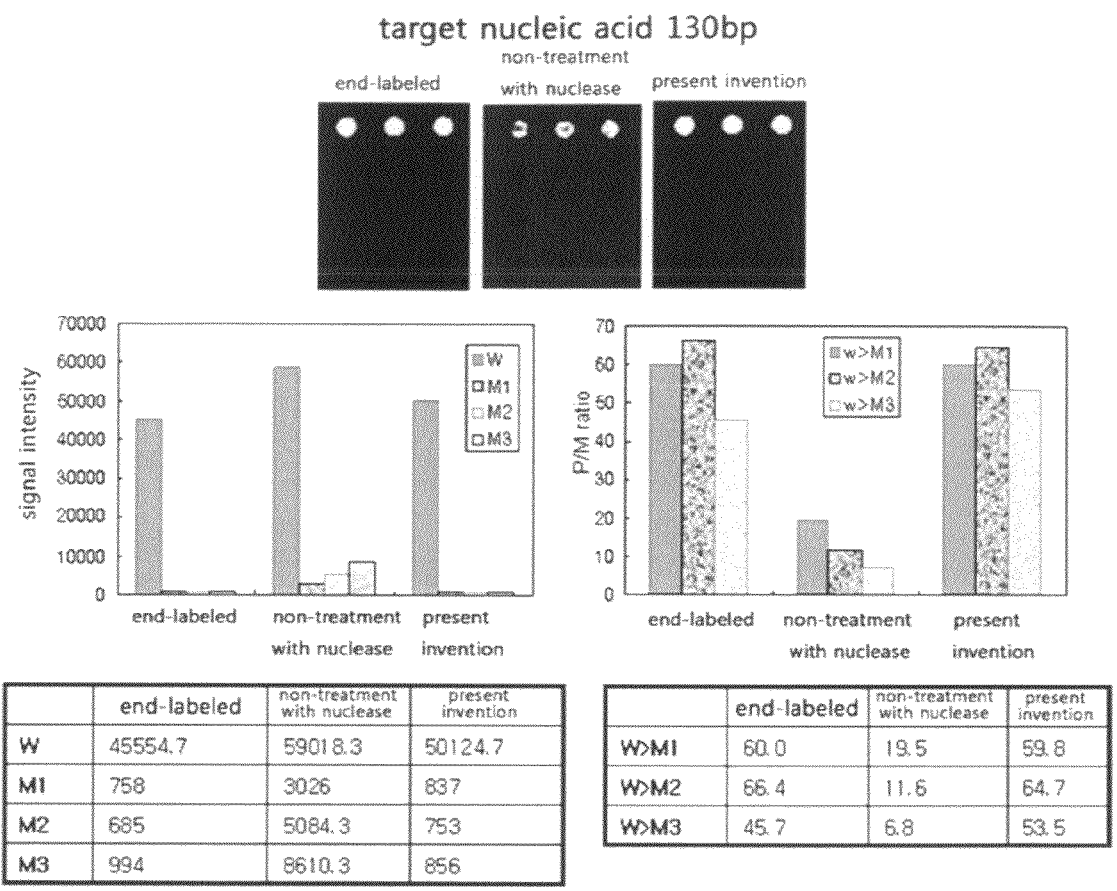

[Figure 8]
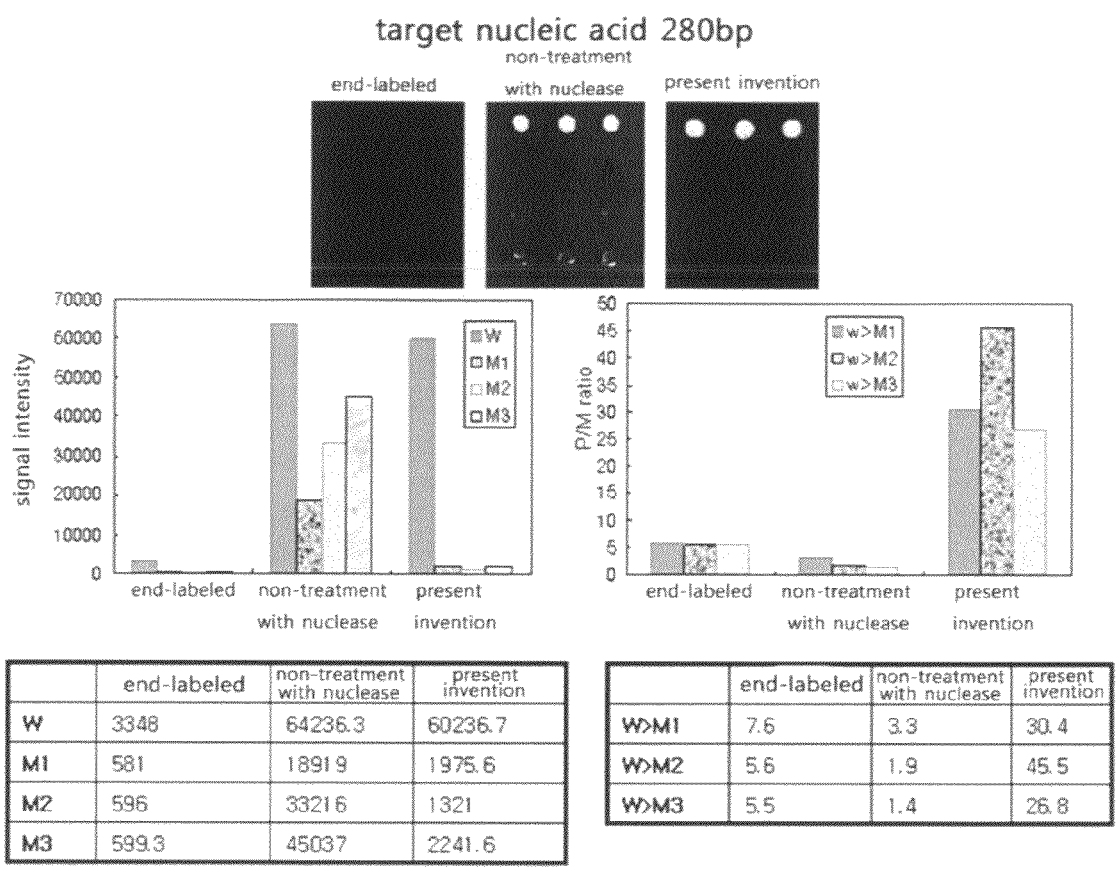

[Figure 9]
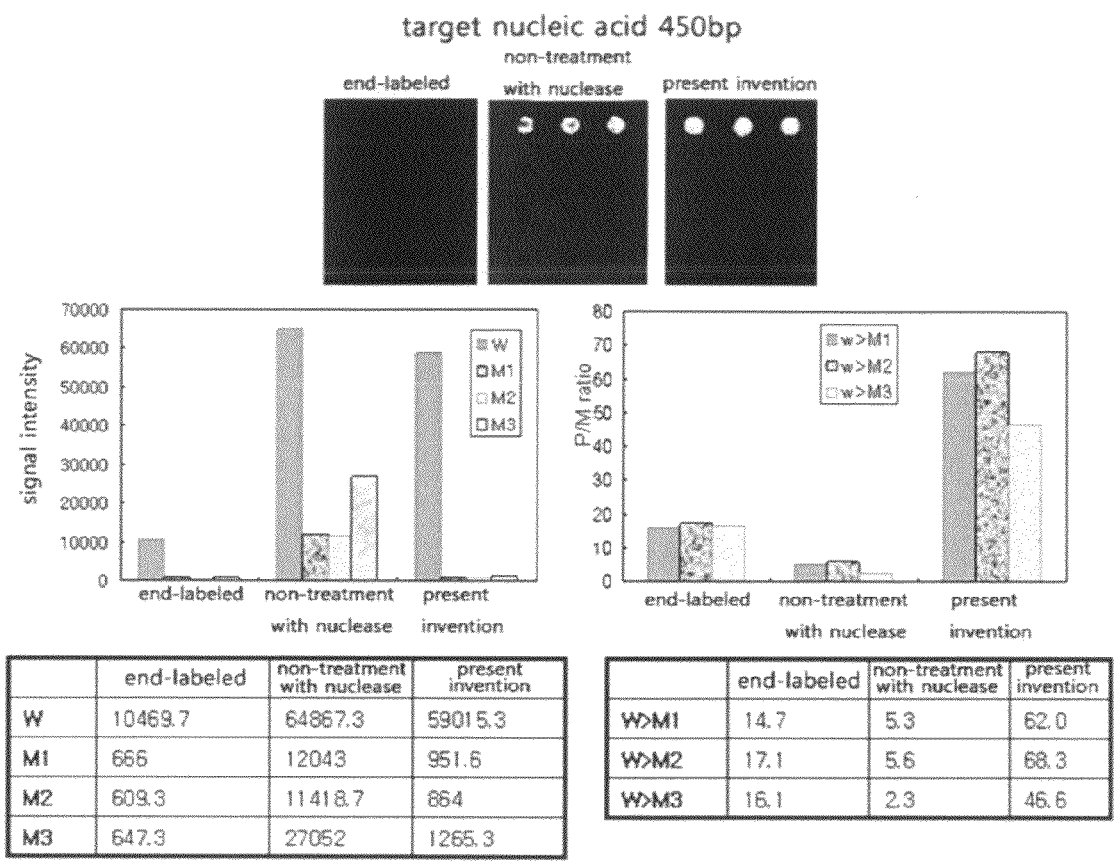

[Figure 10]
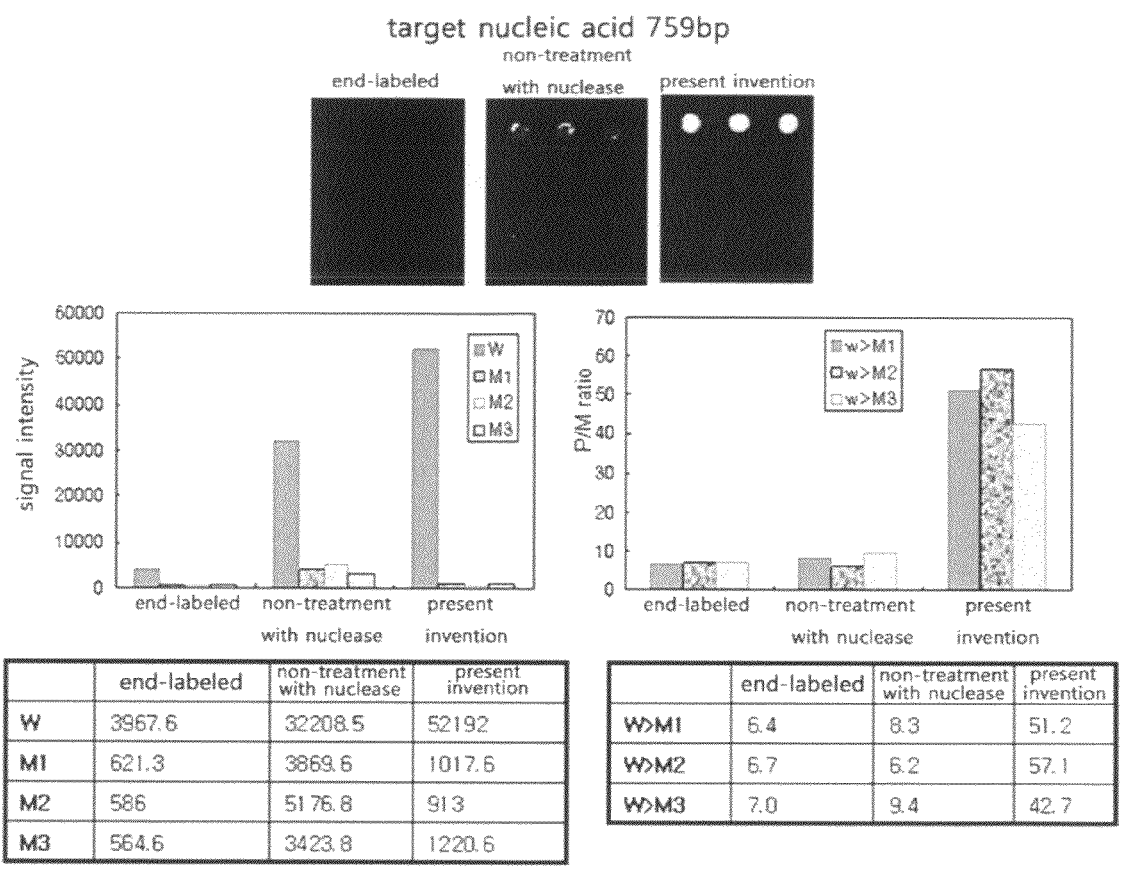

[Figure 11]
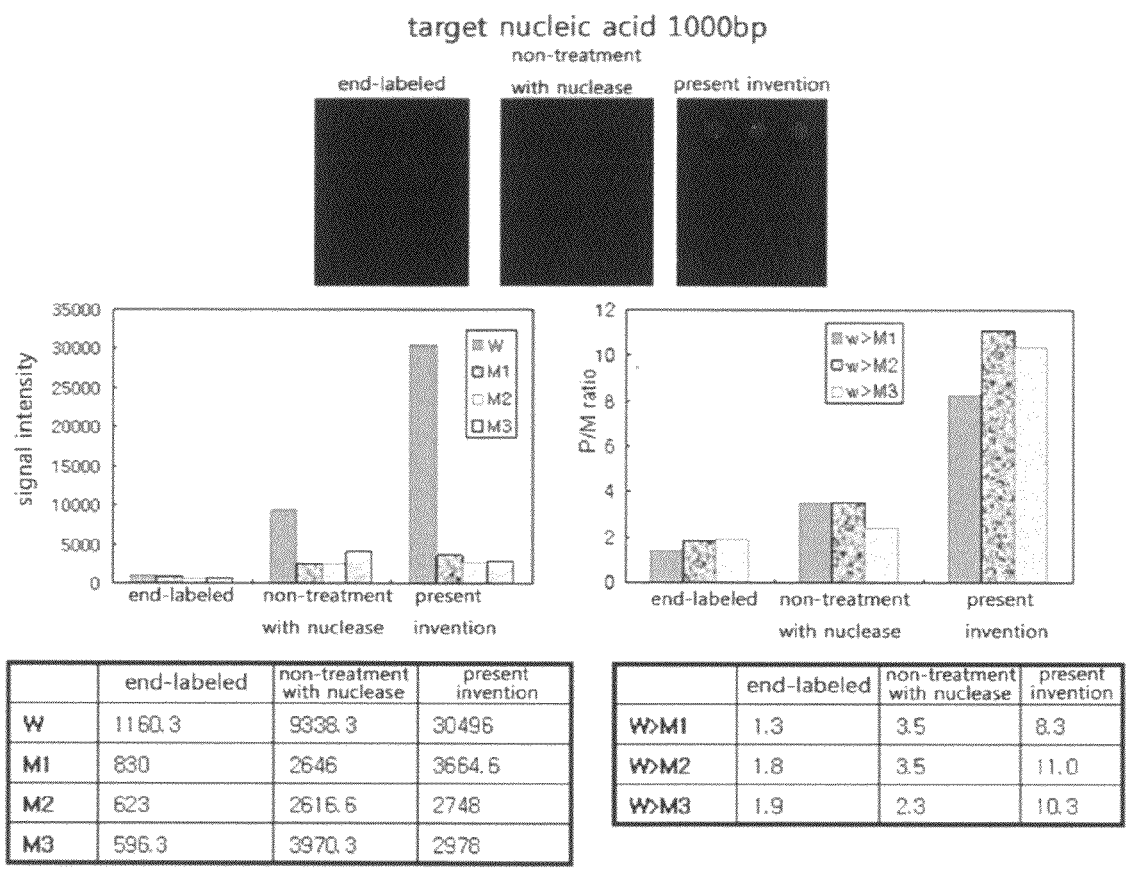

[Figure 12]
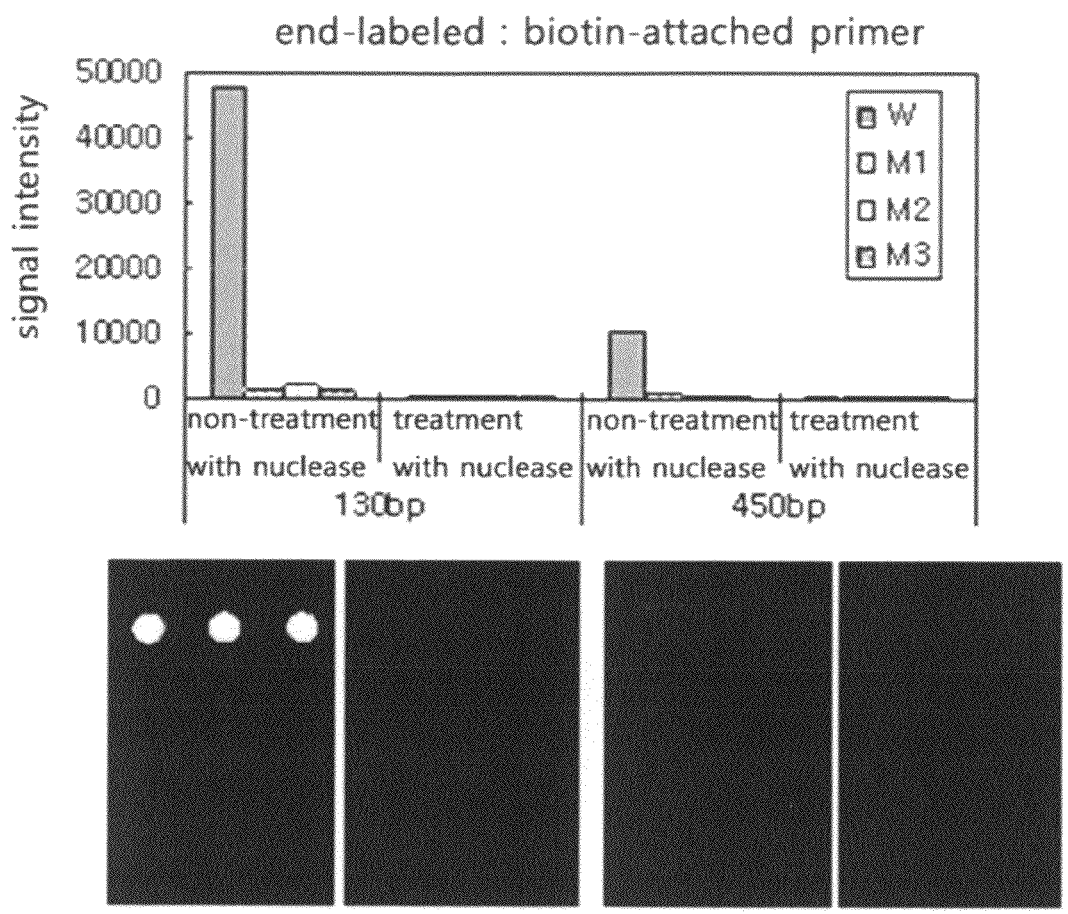

[Figure 13]
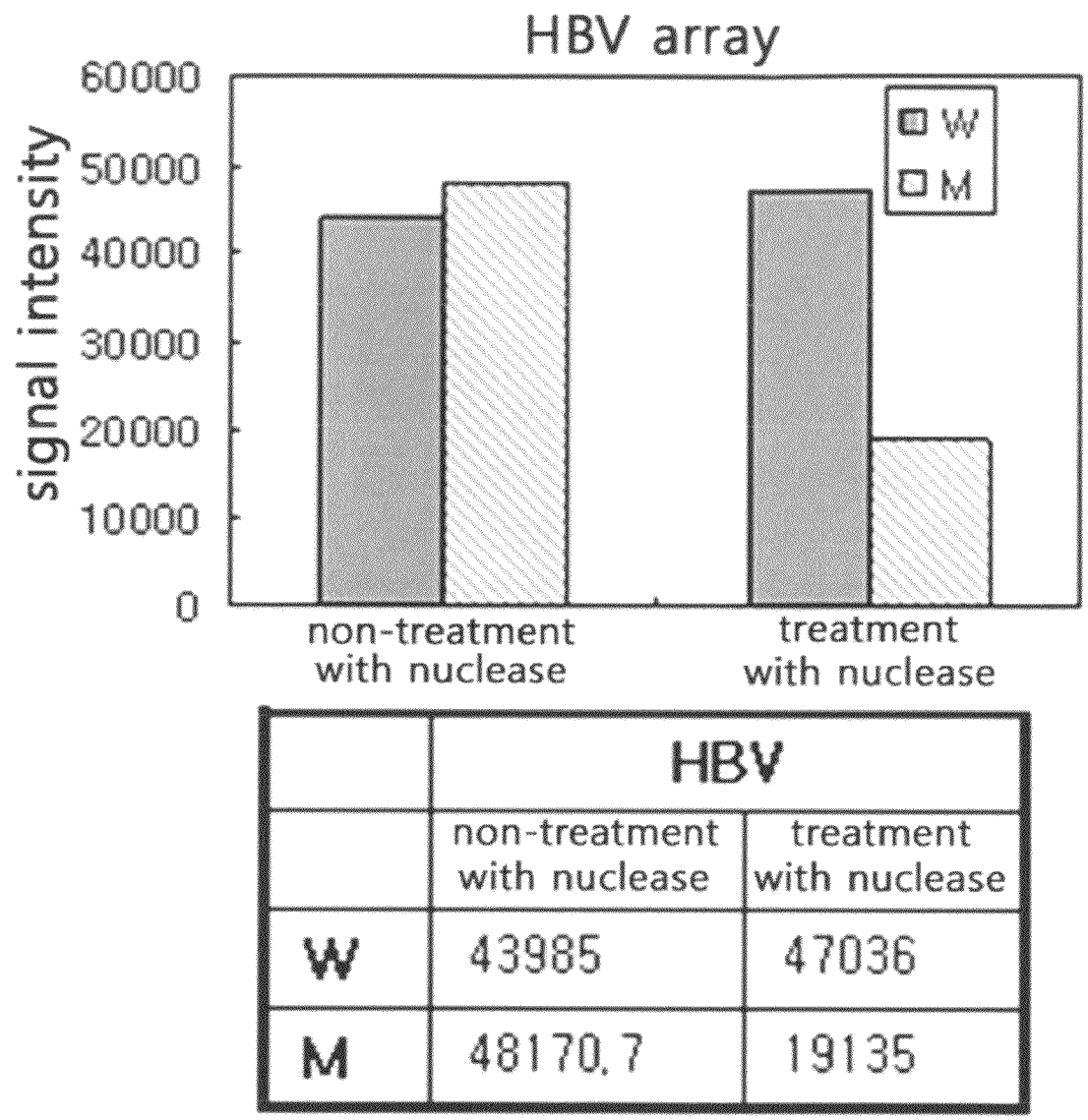

```
                        SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Sense primer of PCR for amplification of target
      nucleic acid

<400> SEQUENCE: 1
tgcaagtcga acggtaacag                                                 20

<210> SEQ ID NO 2
<211> LENGTH: 20
<212> TYPE: DNA
<213> ORGANISM: Artificial Sequence
<220> FEATURE:
<223> OTHER INFORMATION: Antisense primer of PCR for amplification of
      target nucleic acid

<400> SEQUENCE: 2
tgcgacgtta tgcggtatta                                                 20

<210> SEQ ID NO 3
<211> LENGTH: 20
<212> TYPE: DNA
<213> ORGANISM: Artificial Sequence
<220> FEATURE:
<223> OTHER INFORMATION: Antisense primer of PCR for amplification of
      target nucleic acid

<400> SEQUENCE: 3
gtgcaatatt ccccactgct                                                 20

<210> SEQ ID NO 4
```

```
<211> LENGTH: 20
<212> TYPE: DNA
<213> ORGANISM: Artificial Sequence
<220> FEATURE:
<223> OTHER INFORMATION: Antisense primer of PCR for amplification of
      target nucleic acid

<400> SEQUENCE: 4
gttagccggt gcttcttctg                                              20

<210> SEQ ID NO 5
<211> LENGTH: 20
<212> TYPE: DNA
<213> ORGANISM: Artificial Sequence
<220> FEATURE:
<223> OTHER INFORMATION: Sense primer of PCR for amplification of target
      nucleic acid

<400> SEQUENCE: 5
cggttcggtt gaagagaaaa                                              20

<210> SEQ ID NO 6
<211> LENGTH: 21
<212> TYPE: DNA
<213> ORGANISM: Artificial Sequence
<220> FEATURE:
<223> OTHER INFORMATION: Sense primer of PCR for amplification of target
      nucleic acid

<400> SEQUENCE: 6
aaggtataaa gcggggtttt g                                            21

<210> SEQ ID NO 7
<211> LENGTH: 20
<212> TYPE: DNA
<213> ORGANISM: Artificial Sequence
<220> FEATURE:
<223> OTHER INFORMATION: Antisense primer of PCR for amplification of
      target nucleic acid

<400> SEQUENCE: 7
cggggatttc acatctgact                                              20

<210> SEQ ID NO 8
<211> LENGTH: 20
<212> TYPE: DNA
<213> ORGANISM: Artificial Sequence
<220> FEATURE:
<223> OTHER INFORMATION: Sense primer of PCR for amplification of target
      nucleic acid

<400> SEQUENCE: 8
ccatcatctt gggctttcgc                                              20

<210> SEQ ID NO 9
<211> LENGTH: 25
<212> TYPE: DNA
<213> ORGANISM: Artificial Sequence
<220> FEATURE:
<223> OTHER INFORMATION: Antisense primer of PCR for amplification of
      target nucleic acid

<400> SEQUENCE: 9
caaaagaaaa ttggtaacag cggta                                        25

<210> SEQ ID NO 10
<211> LENGTH: 15
<212> TYPE: DNA
```

```
<213> ORGANISM: Artificial Sequence
<220> FEATURE:
<223> OTHER INFORMATION: Probe for E. coli 16S rDNA

<400> SEQUENCE: 10
gcccactcat tacag                                                        15

<210> SEQ ID NO 11
<211> LENGTH: 15
<212> TYPE: DNA
<213> ORGANISM: Artificial Sequence
<220> FEATURE:
<223> OTHER INFORMATION: Probe for E. coli 16S rDNA

<400> SEQUENCE: 11
gcccactgat tacag                                                        15

<210> SEQ ID NO 12
<211> LENGTH: 15
<212> TYPE: DNA
<213> ORGANISM: Artificial Sequence
<220> FEATURE:
<223> OTHER INFORMATION: Probe for E. coli 16S rDNA

<400> SEQUENCE: 12
gcccactaat tacag                                                        15

<210> SEQ ID NO 13
<211> LENGTH: 15
<212> TYPE: DNA
<213> ORGANISM: Artificial Sequence
<220> FEATURE:
<223> OTHER INFORMATION: Probe for E. coli 16S rDNA

<400> SEQUENCE: 13
gcccacttat tacag                                                        15

<210> SEQ ID NO 14
<211> LENGTH: 13
<212> TYPE: DNA
<213> ORGANISM: Artificial Sequence
<220> FEATURE:
<223> OTHER INFORMATION: Probe for HBV lamivudine resistant gene

<400> SEQUENCE: 14
gagccaggta aac                                                          13

<210> SEQ ID NO 15
<211> LENGTH: 13
<212> TYPE: DNA
<213> ORGANISM: Artificial Sequence
<220> FEATURE:
<223> OTHER INFORMATION: Probe for HBV lamivudine resistant gene

<400> SEQUENCE: 15
gagccaagat aac                                                          13
```

METHOD FOR INCREASING EFFICIENCY OR SPECIFICITY OF HYBRIDIZATION BETWEEN PNA PROBES IMMOBILIZED ON SUPPORT AND TARGET NUCLEIC ACIDS

TECHNICAL FIELD

The present invention relates to a technique to increase efficiency or specificity of hybridization between PNA (peptide nucleic acid) probes immobilized on a support and target nucleic acids. More specifically, it relates to a method, a composition and a kit for increasing efficiency or specificity of hybridization of PNA probes, by fragmenting target nucleic acids to reduce the size of target nucleic acids, or by selectively degrading target nucleic acids which mismatch with the PNA probes, by adding nuclease in the hybridization reaction between the PNA probes immobilized on a support and the target nucleic acids.

BACKGROUND ART

Differential gene expression, single nucleotide polymorphisms (SNPs), mutations and genetic information associated with diseases including from pathogenic bacteria and viruses have been elucidated. Those differences or variations in genetic information provide differences between individuals, and determine the development of genetic diseases and susceptibility to diseases. Commonly used techniques for analyzing variation or gene expression include DNA sequencing, RFLP (restriction fragment length polymorphism), allele specific polymerase chain reaction (PCR), southern blot, northern blot, and the like [Present and future of rapid and/or highthroughput methods for nucleic acid testing, Gyorgy csako, 2005, *Clinica Chimica Acta* 1-25]. However, those techniques are time- and cost-consumptive, and labor- and skill-intensive, only one gene or variation can be analyzed at one time, and gel electrophoresis, which is cumbersome, should be involved.

As a novel analysis system which can overcome the drawbacks of the prior genetic analysis methods, DNA chip or DNA microarray technique has been developed [Single nucleotide polymorphism discrimination assisted by improved base stacking hybridization using oligonucleotide microarrays, Wang D. et al., 2003, *Biotechniques*, 35(2), 300-306]. DNA chip has DNA probes designed on the basis of known genetic information immobilized on a solid surface. Typically the hybridization with a target nucleic acid to be analyzed on the chip is detected with fluorescence. By using the DNA chip, a variety of genetic information can be analyzed by a single experiment, so that it is extremely useful for diagnosis of diseases [Development and evaluation of a highly sensitive human papillomavirus genotyping DNA chip, Kim K et al., 2006, *Gynecologic Oncology* 100, 38-43]. DNA chips have been known as the most efficient analysis and diagnosis system among those having been developed hitherto, but still involve technical problems as follows:

First, stability of a DNA chip product is low due to low biological (such as against nuclease, etc.) and chemical (such as against acid, base, etc.) stability of DNA probes.

Second, single nucleotide differences such as SNP, point mutation, etc. can hardly be discriminated with accuracy.

Third, the length of target nucleic acid is limited for hybridization with oligonucleotide probes on a chip.

In using probes immobilized on a support, as in a DNA chip, access to the probes becomes more difficult and so efficiency of hybridization is reduced, as the size of the target nucleic acid is increased. Thus, target nucleic acid, which is not too much long, should be applied to the hybridization. If the length of the target nucleic acid is about 200 base pairs (bp) or longer, the efficiency of hybridization abruptly decreases to reduce perfect match signal, and thus, discrimination from background signal is not easy. The target nucleic acid with the length of longer than 400 bp generates almost no perfect match signal, and so cannot be analyzed [Optimization of fragmentation conditions for microarray analysis of viral RNA, Martin et al., 2005, Analytical biochemistry, 347, 316-323; and Correlation between microarray DNA hybridization efficiency and the position of short capture probe on the target nucleic acid, Regis et al., 2005, BioTechniques, 39, 89-96]. In order to overcome the problems, amplification as separated short fragments when the targets are scattered, long-size amplification followed by fragmentation with restriction enzyme, and amplification of genome followed by small-size amplification with individual specific primers, or the like has been employed [Toward genome-wide SNP genotyping, Ann-Christine Syvanen, 2005, *Nature genetics*, 37, S5-S10; and Assessing Genetic Variation: Genotyping Single Nucleotide Polymorphism, Ann-Christine Syvanen, *Nature*, 2001, 2, 930-942]. However, those are cumbersome and inefficient, requiring much time and effort and high cost for manufacturing the target nucleic acid into small fragments which are capable of hybridization. Further, non-specific signal may be increased from reaction with unreacted residual target nucleic acids.

Various DNA analogues have been developed to overcome instability of DNA itself. Among them, PNA (peptide nucleic acids) was developed by Neilson in 1991 [Peptide nucleic acid, PNA, sequence-selective recognition of DNA by strand displacement with a thymine-substituted polyamide, P. E. Neilson et al., 1991, *Science*, 254, 1497-1500]. As shown in FIG. 1, phosphodiester bond of DNA has been replaced by peptide bond in PNA. PNA comprises adenine, thymine, guanine and cytosine as DNA, so that PNA can base specifically hybridize with DNA or RNA. In particular, differently from natural nucleic acids which electrically repel one another due to phosphate backbone having negative charge, PNA has peptide backbone having no charge, and thus, as compared with DNA, it forms stronger bond with DNA upon hybridization, and the bond is not influenced by salt concentration. Further, since PNA is not degraded by biological degrading enzymes such as nuclease and protease, it is more stable than DNA or RNA. Thus, PNAs, which can complementarily bind with natural nucleic acids, and has high binding strength and stability upon hybridization, have been utilized in genetic analysis or diagnosis [PNA for rapid microbiology, Stender H et al., 2002, *Journal of Microbiological Methods*, 48, 1-17], [Peptide nucleic acids on microarrays and other biosensors, Brandt O et al., 2004, *Trends in Biotechnology*, 22, 617-622; and Detection of target DNA using fluorescent cationic polymer and peptide nucleic acid probes on solid support, Frdric R Raymond et al., 2005, *BMC technology*, 5, 1-5].

As studies taking advantage of the biological stability of PNA was reported a process for discriminating SNP by means of FRET (fluorescence resonance energy transfer), wherein a cationic polymer is bound with an anion of DNA upon the hybridization of PNA and DNA, while the mismatched region between PNA and DNA, if any, is removed by S1 nuclease, one of nucleases [SNP detection using peptide nucleic acid probes and conjugated polymers: Applications in neurodegenerative disease identification, Brent S et al., 2005, *Proceedings of the National Academy of Sciences* 102, 34-39]. Further, a process has been reported, wherein one or two PNA probe(s) is (are) hybridized with a target nucleic acid in a microtube, and then, treated with nuclease to remove the target nucleic acids with the base sequence mismatching with PNA probes, and a fluorophore is attached to target nucleic acids completely hybridized with PNA probes, to observe with naked eyes or mass spectrometry [Detection of single nucleotide polymorphisms by the combination of nuclease S1 and PNA. Sheng Ye et al., 2002, Nucleic Acid Research Supplement No. 2, 235-236; and PNA for one base differentiating protection of DNA from nuclease and its use for SNP detection. Makoto Komiyama et al., 2002, *Journal of American Chemical Society* 2003, 125, 3758-3762].

However, according to the above-described processes, hybridization is performed in a homogeneous solution, and thus, it occurs regardless of the size of the target nucleic acid. According to the processes, nuclease is simply added after hybridization to remove the mismatched region between target nucleic acids and PNA probes, thereby increasing the specificity. In those processes, a target nucleic acid with long length was not used since one or two PNA probes was (were) used at one time to analyze one genetic variation at one time.

Korean Patent Registration No. 436554 (issued on Jun. 8, 2004) disclosed a process for increasing the detection sensitivity of hybridized nucleic acid by applying nuclease to a conventional DNA chip. The process involves removing unhybridized single stranded DNA probes among the immobilized DNA probes, by using nuclease. Specifically, the process involves removing unhybridized DNA probes with the immobilized 5'-terminal on the substrate and the exposed 3'-terminal hydroxyl group, by using exonuclease I which cannot recognize the terminal of a double stranded DNA but can recognize only the 3'-terminal of a single stranded DNA, and hydrolyze only a single stranded DNA with 3'-terminal OH group. Thus, the process is completely different from fragmentation or selective degradation of target nucleic acids by using nuclease. This process may reduce non-specific signal from background signal, but cannot reduce non-specific signal from single nucleotide mismatch. Accordingly, the process can be hardly applied to detect SNP or mutation.

DISCLOSURE

Technical Problem

In order to solve the problems of conventional techniques as mentioned above, the present inventors found that, single nucleotide polymorphism (SNP) can be detected with higher reliability and specificity than that of conventional DNA chips, by employing PNA stable against nuclease as probes and removing with nuclease the region of target nucleic acid which is not hybridized with PNA probes, without degrading the PNA probes immobilized on a support. Further, they found that, if nuclease is incorporated to the hybridization reaction between target nucleic acids with various lengths and PNA probes, hybridization efficiency is increased even with long target nucleic acids, so that they can be applied to a chip without any complicated amplification or pretreatment, and the variation of desired region can be selected with high perfect match signal and specificity, and thus, completed the invention.

Therefore, an object of the present invention is to provide a process for increasing efficiency or specificity of hybridization between PNA probes immobilized on a support and target nucleic acids. The process according to the invention can be widely applied to analysis of mutation, SNP, genotype, gene expression or splice-mutants, epigenetic analysis, resequencing, or the like, with various sizes of target nucleic acids.

Another object of the invention is to provide a composition for increasing efficiency or specificity of hybridization between PNA probes immobilized on a support and target nucleic acids.

Still another object of the invention is to provide a kit for increasing efficiency or specificity of hybridization between PNA probes immobilized on a support and target nucleic acids.

Technical Solution

One aspect of the invention provides a process for increasing efficiency or specificity of hybridization between PNA probes immobilized on a support and target nucleic acids, which comprises the step of fragmenting the target nucleic acids with nuclease to reduce the size of target nucleic acids, or selectively degrading the target nucleic acids which mismatch with the PNA probes, in the hybridization reaction between the PNA probes supported on a support and the target nucleic acids.

Another aspect of the invention provides a composition for increasing efficiency or specificity of hybridization between PNA probes immobilized on a support and target nucleic acids, which comprises nuclease as an active ingredient.

Still another aspect of the invention provides a kit for detecting nucleic acid, which comprises:
i) a plurality of PNA probes immobilized on a support; and
ii) nuclease.

DESCRIPTION OF DRAWINGS

FIG. 1 shows the difference of basic structures of DNA and PNA;

FIG. 2 shows the principle of increasing hybridization specificity by using nuclease on a PNA oligo-chip according to one embodiment of the invention;

FIG. 3 shows the principle of increasing hybridization specificity of a target nucleic acid with long length by using nuclease on a PNA oligo-chip according to one embodiment of the invention;

FIG. 4 shows the base sequences of the target nucleic acids for various sizes (*E. coli* 16S rDNA), and position of probes and primers, employed in the invention;

FIG. 5 shows the results of electrophoresis on 1.5% agarose gel after amplification of target nucleic acids with various sizes (*E. coli* 16S rDNA);

FIG. 6 shows spot arrangement of fluorescence image on a PNA oligo-chip;

FIGS. 7 to 11 show the fluorescence images and quantitative analysis data for the hybridization on a PNA oligo-chip, with end-labeled, biotinyl-dCTP labeled, and biotinyl-dCTP labeled and nuclease treated target nucleic acids (*E. coli* 16S rDNA) (FIG. 7: 130 bp, FIG. 8: 280 bp, FIG. 9: 450 bp, FIG. 10: 759 bp, FIG. 11: 1000 bp);

FIG. 12 shows the quantitative analysis data of the detected signal of end-labeled target nucleic acids (*E. coli* 16S rDNA, 130 bp and 450 bp), without and with addition of nuclease; and FIG. 13 shows the quantitative analysis data of the detected signal of biotinyl-dCTP labeled target nucleic acids (HBV lamivudine-resistant gene), without and with addition of nuclease.

BEST MODE

Other and further objects, features and advantages of the invention will appear more fully from the following description.

Hereinafter, the present invention will be described in detail.

The present invention relates to a technique to increase the efficiency or specificity of hybridization of PNA probes immobilized on a support with target nucleic acids, and to reduce non-specific binding of the probes with target nucleic acids with mismatched nucleotide sequence. According to the present invention, in using PNA probes immobilized on a support, for target nucleic acids with various lengths, single stranded region unhybridized with the PNA probes or mismatched region incompletely complementary to the PNA probes is hydrolyzed with nuclease. The nuclease can be added simultaneously with the hybridization, or after the hybridization is completed. When the nuclease is added simultaneously with the hybridization between PNA probes and target nucleic acids, the length of target nucleic acids is decreased and the efficiency of hybridization is increased. In addition, other regions than those hybridized with PNA probes in the target nucleic acid are hydrolyzed, thereby increasing the specificity. As a result, target nucleic acids of long length, which could not have been detected with the conventional processes, can be detected with PNA probes immobilized on a support, and a plurality of single nucleotide polymorphisms and mutations contained in the long target nucleic acids can be also detected. In order to attain only the increase in hybridization specificity without increase in hybridization efficiency, nuclease may be added after hybridization of target nucleic acids is completed. In case of adding nuclease after hybridization of target nucleic acids is completed, the length of the target nucleic acids is preferably not longer than 400 bp, for example, from 20 to 400 bp, since hybridization efficiency may be decreased with too long target nucleic acids.

According to the invention, in order to apply the reaction of target nucleic acid with nuclease to a PNA chip with immobilized PNA probes, PNA oligomers of Sequence ID Nos. 10 to 15 were immobilized on the surface of a glass slide to manufacture a PNA chip, and nuclease was added thereto to investigate the properties. PNA oligomer of Sequence ID No. 10 is a probe which perfectly matches with the target nucleic acid of E. coli 16S rDNA, while PNA oligomers of Sequence ID Nos. 11 to 13 are probes designed to have one different base from Sequence ID No. 10. PNA oligomer of Sequence ID No. 14 is a probe (180w) which perfectly matches with the target nucleic acid of Hepatitis B virus (HBV) lamivudine-resistant gene, while Sequence ID No. 15 is a probe (180t) designed to have one different base from Sequence ID No. 14. Sequence ID Nos. 14 and 15 could not have specifically detected the target nucleic acid due to very strong non-specific signal in conventional chips.

TABLE 1

| Sequence No. | Sequence Designation | Sequence (5'→3') | Description |
|---|---|---|---|
| 10 | E. coli W | GCCCACTCATTACAG | Probe of E. coli 16S rDNA |
| 11 | E. coli M1 | GCCCACTGATTACAG | Mismatch at $8^{th}$ base (C→G) |
| 12 | E. coli M2 | GCCCACTAATTACAG | Mismatch at $8^{th}$ base (C→A) |
| 13 | E. coli M3 | GCCCACTTATTACAG | Mismatch at $8^{th}$ base (C→T) |

TABLE 1-continued

| Sequence No. | Sequence Designation | Sequence (5'→3') | Description |
|---|---|---|---|
| 14 | HBV W | GAGCCAGGTAAAC | Probe of HBV lamivudine-resistant gene |
| 15 | HBV M | GAGCCAAGATAAC | Mismatch at $7^{th}$ base (G→A) |

A PNA chip was manufactured by immobilizing the PNA oligomers on a glass slide with exposed epoxy functional groups.

In the present invention, in order to elucidate the action of nuclease, target nucleic acids were utilized as follows:

1) In order to examine whether the target nucleic acid which had been difficult to analyze on conventional DNA chips can be analyzed, 5 target nucleic acids with different lengths, i.e. E. coli 16S rDNA of 130, 280, 450, 759 and 1000 bp were amplified and used.

2) In order to examine the discriminability of point mutation, target nucleic acids of HBV lamivudine-resistant mutant and wild-type, having one different base sequence, were amplified and used.

According to the invention, the perfect match signal and signal discriminability of hybridization with PNA probes immobilized on a support were compared, according to:

1) a process wherein 5'-terminal of primer (see Table 2) is labeled with a detectable label and amplified, and hybridization is performed with or without addition of nuclease and detected;

2) a process wherein dNTP labeled with a detectable label is added to a reaction mixture for PCR to label target nucleic acids during the amplification, and hybridization is performed without addition of nuclease and detected; and 3) a process wherein dNTP labeled with a detectable label is added to a reaction mixture for PCR to label target nucleic acids during the amplification, and hybridization is performed with addition of nuclease and detected.

The processes of 1) to 3) generally comprise the steps of:
  a) preparing target DNA;
  b) performing hybridization reaction of probe PNA with target DNA;
  c) washing to remove the residual reactant after hybridization reaction; and
  d) detecting the signal from the formation of PNA/DNA hybrid.

In case of detecting hybridization by fluorescence, in step a), the end labeling of the primer (process 1) is not desirable because the primer is hydrolyzed upon treatment with nuclease and so it is difficult to detect fluorescence (see FIGS. 7 to 12). It is preferable to directly attach fluorophore to dNTP, i.e. dATP, dCTP, dGTP, dTTP, for example, dCTP, employed for PCR, or to attach a substance, for example, biotin, which can react with fluorophore (process 3).

Labels that can be used are not particularly limited. Examples thereof include biotin, rhodamine, cyanine 3, cyanine 5, pyrene, cyanine 2, green fluorescent protein (GFP), calcein, fluorescein isothiocyanate (FITC), Alexa 488, 6-carboxy-fluorescein (FAM), 2',4',5',7'-tetrachloro-6-carboxy-4,7-dichlorofluorescein (HEX), 2',7'-dichloro-6-carboxy-4,7-dichlorofluorescein (TET), fluorescein chlorotriazinyl, fluorescein, Oregon green, magnesium green, calcium green, 6-carboxy-4',5'-dichloro-2',7'-dimethoxyfluorescein (JOE), tetramethylrhodamine, tetramethyl-rhodamine isothiocyanate (TRITC), carboboxytetramethyl rhodamine (TAMRA), rhodamine phalloidin, Pyronine Y, Lissamine, X-rhodamine (ROX), calcium crimson, Texas red, Nile red and thiadicarbocyanine.

In case of detecting the hybridization by other than fluorescence (see the following descriptions on step d), such a labeling step can be omitted.

Amplification methods of target nucleic acids, which can be used in the invention, are not particularly limited. Examples thereof include branched DNA (bDNA) amplification, hybrid capture, ligase chain reaction (LCR), polymerase chain reaction (PCR), nucleic acid sequence based amplification (NASBA), reverse transcription-polymerase chain reaction (RT-PCR), strand displacement amplification (SDA), transcription-mediated amplification (TMA), rolling circle amplification (RCA), and the like.

Step b) is a conventional hybridization reaction. If nuclease is added to a hybridization buffer, target nucleic acids with long length, for example, of 200~20,000 bp, particularly, of 200~5,000 bp, are cleaved by nuclease to facilitate the access to probes, thereby to increase the hybridization efficiency (see FIG. 3).

Step c) is carried out according to conventional washing process. In case of adding nuclease in step c), this increases specificity of hybridization (see FIG. 2). Specifically, target nucleic acids having completely complementary sequence form complete double strands with PNA probes, but target nucleic acids with one mismatched nucleotide sequence hybridize only in complementary regions to form double strands with PNA probes, while remaining single strands in non-complementary regions, to form partially hybridized state. If a DNase specific to single stands is added thereto, the completely hybridized double stranded region is not hydrolyzed, while the incompletely hybridized target nucleic acid is hydrolyzed, so that only the completely hybridized target nucleic acid can be selected. Since DNA probe itself can be hydrolyzed by nuclease in a DNA chip with immobilized DNAs, this cannot be applied to the DNA chip. Thus, the present invention employs PNA stable against nuclease. As shown in FIG. 1, due to a very high stability of PNA against nuclease, nuclease cannot recognize the completely hybridized region between PNA and DNA to maintain strong bond, while the bond between PNA and DNA with one nucleotide mismatch is unstable, and so nuclease recognizes and hydrolyzes the target DNA. Consequently, only the completely complementarily bound region between PNA and DNA remains on the PNA chip.

Nucleases that can be used in the present invention are not particularly limited. DNase 1, exonuclease or endonuclease can be used alone, or in combination. Specific examples of exonuclease or endonuclease include exonuclease 1, S1 nuclease, mung bean nuclease, ribonuclease A, ribonuclease T1, nuclease P1, and so on. Restriction enzyme, which cleaves a specific base sequence in nucleic acids, can be used for this purpose. Particularly, S1 nuclease is widely used nuclease, which can hydrolyze single stranded nucleic acids and double stranded nucleic acids with nicks, as well as heteroduplex DNA with a loop or a gap [Purification and Properties of S1 Nuclease from *Aspergillus*, Vogt V M, 1980, *Methods in Enzymology*, 65, 248-255]. By using such property, target nucleic acids with one nucleotide mismatch forming a nick can be removed, and variations of single nucleotide difference can be accurately discriminated.

Step d) can be carried out according to conventional hybridization detection methods including fluorescence detection, electric methods, electrochemical methods, detection of mass change, detection of electric charge change, or detection of change in optical properties [DNA biosensors based on Peptide Nucleic Acid (PNA) recognition layers, Wang J, 1998, *Biosensors and Bioelectronics*, 13, 757-762; Labelfree fully electronic nucleic acid detection system based on a field-effect transistor device, Uslu F et al., 2004, *Biosensors and Bioelectronics*, 19, 1723-1731; Direct ultrasensitive electrical detection of DNA and DNA sequence variations using nanowire nanosensors, Hahm J and Lieber C M, 2004, *Nano Letters*, 4, 51-54; Impedance-based detection of DNA sequences using a silicon transducer with PNA as the probe layer, A. Macanovic et al. 2004, *Nucleic Acids Research*, 32, e20; S. Manalis and T. Burg, U.S. Pat. No. 7,282,329 "Suspended microchannel detectors"; and P. Warthoe and S. Iben, US Patent Application Publication 2004/0072208 A1 "Surface acoustic wave sensors and method for detecting target analytes"].

According to the process of the invention (e.g. the above process 3), even a single nucleotide difference, which has been difficult to discriminate, can be accurately discriminated, and so false negative and positive data can be reduced in a diagnosis chip to greatly increase the reliability. Further, target nucleic acids of large size, which have been limited for use in conventional oligo-chips, can be used, and target nucleic acids of various sizes can be employed without limitation. In addition, target nucleic acids can be labeled with various detectable labels, and thus, the invention can be applied to any processes to discriminate single strand and double strand by nucleic acid hybridization.

A composition according to the invention, which comprises nuclease as an active ingredient, can be used to increase efficiency or specificity of hybridization between PNA probes immobilized on a support and target nucleic acid.

A kit for detecting nucleic acid according to the present invention, which comprises a plurality of PNA probes immobilized on a support and nuclease, can be used to detect a plurality of SNPs and mutations contained in the target nucleic acids. The kit according to the invention may contain at least three PNA probes. The kit for detecting SNPs and mutations in total genome may contain several tens or hundreds of thousand PNA probes.

EXAMPLES

Hereinafter, the present invention will be described in more detail with reference to the following examples, which are provided only for the better understanding of the present invention but should not be construed to limit the scope of the present invention in any manner. It would be apparent to a person having an ordinary skill in the art that various alterations and modifications can be made within the spirit and scope of the invention.

Preparation 1

Synthesis of Primers for Preparing Target Nucleic Acids

For the preparation of target nucleic acids according to the invention, primers for PCR were synthesized. The primer sequences were selected from five *E. coli* 16S rDNAs having different sizes as shown in Table 2. Further, they were selected from lamivudine-resistant gene in hepatitis B virus, as shown in Table 3. The primers for PCR were synthesized by Bioneer (Korea) as two types, ones without biotin and ones with biotin attached at 5'-terminal.

TABLE 2

| | Base sequence of primer (5'→3') | Size of PCR product (bp) |
|---|---|---|
| EC1 Sense (SEQ ID No. 1) | TGC AAG TCG AAC GGT AAC AG | 130 |
| Antisense (SEQ ID No. 2) | TGC GAC GTT ATG CGG TAT TA | |
| EC2 Sense (SEQ ID No. 1) | TGC AAG TCG AAC GGT AAC AG | 280 |
| Antisense (SEQ ID No. 3) | GTG CAA TAT TCC CCA CTG CT | |
| EC3 Sense (SEQ ID No. 1) | TGC AAG TCG AAC GGT AAC AG | 450 |
| Antisense (SEQ ID No. 4) | GTT AGC CGG TGC TTC TTC TG | |
| EC4 Sense (SEQ ID No. 5) | CGG TTC GGT TGA AGA GAA AA | 759 |
| Antisense (SEQ ID No. 4) | GTT AGC CGG TGC TTC TTC TG | |
| EC5 Sense (SEQ ID No. 6) | AAG GTA TAA AGC GGG GTT TTG | 1000 |
| Antisense (SEQ ID No. 7) | CGG GGA TTT CAC ATC TGA CT | |

TABLE 3

| | Base sequence of primer (5'→3') | Size of PCR product (bp) |
|---|---|---|
| HBV-F Sense (SEQ ID No. 8) | CCA TCA TCT TGG GCT TTC GC | 200 |
| HBV-R Antisense (SEQ ID No. 9) | CAA AAG AAA ATT GGT AAC AGC GGT A | |

Preparation 2

Preparation of Target Nucleic Acids by PCR Using Biotinylated Primers

DNA extracted from *E. coli* KCTC 1112 which was obtained from Korean Collection for Type Cultures was used as template DNA. The DNA was amplified by performing PCR with the following conditions:

Denaturation at 94° C. for 5 minutes; 30 cycles of denaturation at 94° C. for 1 minute, annealing at 55° C. for 1 minute and extension at 72° C. for 1 minute; and final extension at 72° C. for 5 minutes, for a reaction mixture consisting of 2 μl of template DNA solution (50 ng/μl), each 1 μl of five types of biotinylated sense primers (20 pmol/μl) and biotinylated antisense primers (20 pmol/μl) as shown in Table 2, 3 μl of dNTP (25 mM), 5 μl of 10× Taq buffer (containing MgCl$_2$), 5 μl of 0.2% BSA (bovine serum albumin), 0.2 μl of Taq (5 U/μl, Solgent, Korea), and 36.8 μl of distilled water.

Upon the completion of the reaction, to 5 μl of the PCR product (130 bp, 280 bp, 450 bp, 759 bp, 1000 bp) was added 1 μl of gel loading buffer (Sunbio, Korea), and the mixture was subjected to electrophoresis on 1.5% agarose gel, followed by staining with 1 μg/ml of ethidium bromide (EtBr), and the product was confirmed under a UV-transilluminator. The base sequences of target nucleic acids with different sizes and the positions of the probes and primers are shown in FIG. 4. The results of electrophoresis are shown in FIG. 5.

Preparation 3

Preparation of Target Nucleic Acids by PCR Using Biotinyl-dCTP

DNA extracted from *E. coli* KCTC 1112 which was obtained from Korean Collection for Type Cultures was used as template DNA. The DNA was amplified by performing PCR with the following conditions:

Denaturation at 94° C. for 5 minutes; 30 cycles of denaturation at 94° C. for 1 minute, annealing at 55° C. for 1 minute and extension at 72° C. for 1 minute; and final extension at 72° C. for 5 minutes, for a reaction mixture consisting of 2 μl of template DNA solution (50 ng/μl), each 1 μl of five types of sense primers (20 pmol/μl) and antisense primers (20 pmol/μl) as shown in Table 2, 2.45 μl of dNTP (25 mM), 4 μl of 11-biotinyl-dCTP (1 mM), 5 μl of 10× Taq buffer (containing MgCl$_2$), 5 μl of 0.2% BSA (bovine serum albumin), 0.2 μl of Taq (5 U/μl, Solgent, Korea), and 32.8 μl of distilled water.

Upon the completion of the reaction, to 5 μl of the PCR product (130 bp, 280 bp, 450 bp, 759 bp, 1000 bp) was added 1 μl of gel loading buffer (Sunbio, Korea), and the mixture was subjected to electrophoresis on 1.5% agarose gel, followed by staining with 1 μg/ml of ethidium bromide (EtBr), and the product was confirmed under a UV-transilluminator. The base sequences of target nucleic acids with different sizes and the positions of the probes and primers are shown in FIG. 4. The results of electrophoresis are shown in FIG. 5.

Preparation 4

Manufacture of PNA Chip

The purified PNA oligomers of Sequence ID Nos. 10 to 13 as shown in Table 1 were diluted in PANArray™ spotting buffer (Panagene, Korea) to a concentration of 50 mM, and spotted on a glass slide functionalized with epoxy group by pin-spotting method, and the slide was allowed to stand at ambient temperature for 4 hours while maintaining 75% humidity. Then, it was introduced to dimethylformamide (DMF), and washed with ultrasonication for 15 minutes. Then, it was introduced to DMF containing 0.1 M succinic anhydride. The reaction was performed at 40° C. for 2 hours to remove residual amine groups. It was washed with DMF for 15 minutes, and washed with deionized water with ultrasonication for 15 minutes. Then, 100 mM of Tris-HCl containing 0.1 M ethanolamine was added thereto and reaction was performed at 40° C. for 2 hours to inactivate the residual epoxy groups on the solid surface. It was washed with deionized water for 5 minutes, and dried.

Comparative Example 1

Hybridization of Target Nucleic Acids Amplified with Biotin-Labeled Primers

FIG. 4 shows the base sequences of the target nucleic acids for various sizes (*E. coli* 16S rDNA), and position of probes and primers, employed in the invention; (1) SEQ ID No. 1, (2) complementary position of SEQ No. 10, (3) complementary position of SEQ ID No. 2, (4) complementary position of SEQ ID No. 3, (5) complementary position of SEQ ID No. 4, (6) SEQ ID No. 5, (7) SEQ ID No. 6, (8) complementary position of SEQ ID No. 7.

Five (5) μl of PCR product end-labeled with biotin was introduced to 100 μl of PANArray™ hybridization buffer (Panagene, Korea). Streptavidine-Cy5 was added thereto to cause fluorescent reaction. Onto a glass slide was injected 100 μl of hybridization buffer, and reaction was performed at 40° C. for 2 hours. Upon the completion of the reaction, the slide was washed twice with PANArray™ washing buffer (Panagene, Korea) at ambient temperature for 5 minutes, and dried (nuclease non-treated group). For the nuclease treated group, 0.5 μl (1 U/μl) of S1 nuclease (Amersham Biosciences, U.S.A.) in 100 μl of reaction buffer was injected onto the dried slide, reaction was performed at 37° C. for 1 hour, and then, washed and dried as described above. The image of the slide was analyzed by using a fluorescence scanner (Genepix 4000B, Exon, U.S.A.). The results are shown in FIGS. 7 to 12.

As shown in FIGS. 7 to 11, in case of 130 bp target nucleic acid, high perfect match signal and perfect match/mismatch ratio (P/M ratio) were shown. However, perfect match signal decreased as the size of the target nucleic acid increased (280 bp, 450 bp, 759 bp, and 1000 bp). Particularly, in case of 1000 bp of target nucleic acid, extremely low perfect match signal was obtained to make the discrimination of perfect match from mismatch difficult (less than 2 of P/M ratio).

In addition, as shown in FIG. 12, in the nuclease treated group, no signal was obtained because the labeled regions of the target nucleic acids had been removed. From the results, it was confirmed that nuclease hydrolyzed the target nucleic acid on the chip.

Comparative Example 2

Hybridization of Target Nucleic Acid Amplified with Biotinyl-dCTP

Five (5) μl of PCR product with biotinyl-dCTP in 100 μl was introduced to PANArray™ hybridization buffer (Panagene, Korea). Onto a slide, 100 μl of hybridization buffer was injected, and reaction was performed at 40° C. for 2 hours. Upon the completion of the reaction, the slide was washed twice with PANArray™ washing buffer (Panagene, Korea) at ambient temperature for 5 minutes, and dried. A mixture of Hybridization buffer (100 μl) and streptavidine-Cy5 was added to the dried slide to cause fluorescent reaction. The slide was filled with hybridization mixture (100 μl), and reaction was performed at 40° C. for 30 minutes. Upon the completion of the reaction, the slide was washed twice with PANArray™ washing buffer at ambient temperature for 5 minutes, and dried. The image of the glass slide was analyzed with a fluorescence scanner (Genepix 4000B, Exon, U.S.A.). The results are shown in FIGS. 7 to 11.

As shown in FIGS. 7 to 11, in case of relatively small target nucleic acids (130 to 450 bp), relatively high perfect match signal could be obtained without addition of nuclease, but discriminability of perfect match and mismatch was relatively low. On the other hand, in case of large target nucleic acids (759 to 1000 bp), perfect match signal decreased and discriminability of perfect match and mismatch remarkably decreased (in case of 1000 bp nucleic acid, P/M ratio was 2.3~3.5).

Example 1

Hybridization of Target Nucleic Acid Amplified with Biotinyl-dCTP and Treatment with Nuclease Five (5) μl of PCR product with biotinyl-dCTP was introduced to 100 μl of PANArray™ hybridization buffer (Panagene, Korea). Onto a slide, 100 μl of the hybridization buffer was injected, and reaction was performed at 40° C. for 2 hours. Upon the completion of the reaction, the slide was washed twice with PANArray™ washing buffer (Panagene, Korea) at ambient temperature for 5 minutes, and dried. Onto the dried slide, 0.5 μl (1 U/μl) of S1 nuclease (Amersham Biosciences, U.S.A.) in 100 μl of reaction buffer was injected, and reaction was performed at 37° C. for 1 hour. Upon the completion of the reaction, it was washed and dried as described above. A mixture of the hybridization buffer (100 μl) and streptavidine-Cy5 was added thereto to cause fluorescent reaction on the dried slide. Hybridization was performed at 40° C. for 30 minutes. Upon the completion of the reaction, the slide was washed twice with PANArray™ washing buffer (Panagene, Korea) at ambient temperature for 5 minutes, and dried. The image of the glass slide was analyzed with a fluorescence scanner (Genepix 4000B, Exon, U.S.A.). The results are shown in FIGS. 7 to 11.

As shown in FIGS. 7 to 11, in the nuclease treated group, the results were not influenced by the target size, i.e. high perfect match signal of signal intensity of 50000 to 60000 was obtained without showing differences among the target nucleic acids from 130 bp up to 759 bp, and P/M ratio, discriminability between perfect match and mismatch, was 8.3 to 11, which was 10-fold higher than that of Comparative Example 1 using the end-labeled target nucleic acid. Further, in case of larger target nucleic acids of 759 to 1000 bp, the nuclease treated group according to the present invention showed higher perfect match signal and at least 3-fold higher discriminability between perfect match and mismatch, than the nuclease non-treated group.

Comparative Example 3 and Example 2

Hybridization on HBV PNA Chip

The following examples were provided to examine the effect of the invention for 180t probes with perfect match and mismatch that could not have been discriminated according to a conventional process.

By using the primer (HBV-F and HBV-R) of Table 3 prepared from Preparation 1 and HBV DNA obtained from Genine (Korea) as a template DNA, the target DNA was amplified according to substantially the same process as in Preparation 3. By using the HBV probes (Sequence ID Nos. 14 and 15) as shown in Table 1, a PNA chip was manufactured according to substantially the same process as that of Preparation 4. Hybridization, or hybridization and nuclease treatment was (were) carried out according to substantially the same process as that of Comparative Example 2 or Example 1. The results are shown in FIG. 13.

In the nuclease non-treated group, the strengths of perfect match and mismatch are almost the same, so that HBV wild type and mutant type could not be discriminated on the PNA chip. On the other hand, in the nuclease treated group, mismatch signal was largely decreased, so that HBV wild type and mutant type could be discriminated (P/M ratio=2.5).

INDUSTRIAL APPLICABILITY

According to the invention, in using PNA probes immobilized on a support, unhybridized target nucleic acids are selectively removed by treating with nuclease simultaneously with or after hybridization of the target nucleic acid, so that sensitivity and specificity of hybridization can be increased to facilitate discrimination of single nucleotide mismatch. By treating with nuclease simultaneously with the hybridization of target nucleic acids, the hybridization efficiency of target nucleic acids of large size can be increased, and thus, analysis of a long target nucleic acid can be carried out without complicated amplification or pretreatment, and a plurality of SNPs or mutations contained in the long target nucleic acid can be detected with a single amplification of the target nucleic acid. Therefore, genes or mutations associated with various diseases can be detected with high sensitivity and specificity within a short time, and SNPs, which could hardly have been discriminated, can be detected with high sensitivity and specificity, to be useful for wide diagnosis of various genes.

SEQUENCE LIST TEXT

Sequence ID No. 1 is the base sequence of EC1, EC2 and EC3 sense primer for amplifying target nucleic acid of *E. coli* 16S rDNA;

Sequence ID No. 2 is the base sequence of EC1 antisense primer for amplifying target nucleic acid of *E. coli* 16S rDNA;

Sequence ID No. 3 is the base sequence of EC2 antisense primer for amplifying target nucleic acid of *E. coli* 16S rDNA;

Sequence ID No. 4 is the base sequence of EC3 and EC4 antisense primers for amplifying target nucleic acid of *E. coli* 16S rDNA;

Sequence ID No. 5 is the base sequence of EC4 sense primer for amplifying target nucleic acid of *E. coli* 16S rDNA;

Sequence ID No. 6 is the base sequence of EC5 sense primer for amplifying target nucleic acid of *E. coli* 16S rDNA;

Sequence ID No. 7 is the base sequence of EC5 antisense primer for amplifying target nucleic acid of *E. coli* 16S rDNA;

Sequence ID No. 8 is the base sequence of HBV-F primer for amplifying target nucleic acid of HBV lamivudine-resistant gene;

Sequence ID No. 9 is the base sequence of HBV-R primer for amplifying target nucleic acid of HBV lamivudine-resistant gene;

Sequence ID No. 10 is the base sequence of PNA probes which perfectly matches the target nucleic acid of 16S *E. coli* rDNA;

Sequence ID Nos. 11 to 13 are the base sequences of PNA probes designed to have one different base from Sequence ID No. 10;

Sequence ID No. 14 is the base sequence of PNA probe (180w) which perfectly matches with the target nucleic acid of HBV lamivudine-resistant gene; and Sequence ID No. 15 is the base sequence of PNA probe (180t) designed to have one different base from Sequence ID No. 14.

The invention claimed is:

1. A process for increasing efficiency or specificity of hybridization between PNA (Peptide Nucleic Acid) probes immobilized on a support and target nucleic acids, which comprises the steps of
   1) hybridizing the PNA probes immobilized on a support to the target nucleic acids, and
   2) fragmenting or selectively degrading the target nucleic acids using one or more nucleases so that the sizes of the target nucleic acids are reduced or nucleic acids in the target nucleic acids which mismatch with the PNA probes are degraded and the efficiency or the specificity of the hybridization between the PNA probes and the target nucleic acids are increased, wherein step (1) and step (2) are simultaneously performed.

2. The process according to claim 1, wherein the sizes of the target nucleic acids are 200 bp to 20,000 bp.

3. The process according to claim 2, wherein the sizes of the target nucleic acids are 200 bp to 5,000 bp.

4. The process according to claim 1, wherein the target nucleic acids are labeled with a detectable label in the regions where the PNA probes are bound therewith.

5. The process according to claim 4, wherein the detectable label is selected from the group consisting of biotin, rhodamine, cyanine 3, cyanine 5, pyrene, cyanine 2, green fluorescent protein (GFP), calcein, fluorescein isothiocyanate (FITC), Alexa 488, 6-carboxy-fluorescein (FAM), 2',4',5',7'-tetrachloro-6-carboxy-4,7-dichlorofluorescein (HEX), 2',7'-dichloro-6-carboxy-4,7-dichlorofluorescein (TET), chlorotriazinyl fluorescein, fluorescein, Oregon green, magnesium green, calcium green, 6-carboxy-4',5'-dichloro-2',7'-dimethoxyfluorescein (JOE), tetramethylrhodamine, tetramethyl-rhodamine isothiocyanate (TRITC), carboboxytetramethyl rhodamine (TAMRA), rhodamine phalloidin, Pyronine Y, Lissamine, X-rhodamine (ROX), calcium crimson, Texas red, Nile red and thiadicarbocyanine.

6. The process according to claim 1, wherein the target nucleic acids are amplified by the method selected from the group consisting of branched DNA (bDNA) amplification, ligase chain reaction (LCR), polymerase chain reaction (PCR), nucleic acid sequence based amplification (NASBA), reverse transcription-polymerase chain reaction (RT-PCR), strand displacement amplification (SDA), transcription-mediated amplification (TMA) and rolling circle amplification (RCA).

7. The process according to claim 1, wherein the nucleases are selected from the group consisting of exonucleases, endonucleases and mixtures thereof.

8. The process according to claim 7, wherein the nucleases are selected from the group consisting of DNase I, exonuclease I, S1 nuclease, mung bean nuclease, restriction enzymes and mixtures thereof when the target nucleic acids are DNA or the nucleases are selected from the group consisting of ribonuclease T1, ribonuclease P1 and mixtures thereof when the target nucleic acids are RNA.

9. The process according to claim 1, the process can be used in the analysis of mutations, single nucleotide polymorphism (SNP), genotypes, gene expression or splice-mutants, or can be used in epigenetic analysis or resequencing a nucleic acid.

10. The process according to claim 1, wherein the hybridization is detected by a fluorescence method, an electric method, or an electrochemical method.

* * * * *